United States Patent
Gossett

[11] 3,950,158
[45] Apr. 13, 1976

[54] UREA COLD PACK HAVING AN INNER BAG PROVIDED WITH A PERFORATED SEAL

[75] Inventor: Rodger L. Gossett, Red Bud, Ill.

[73] Assignee: American Medical Products Company, St. Louis, Mo.

[22] Filed: May 31, 1974

[21] Appl. No.: 475,032

[52] U.S. Cl. .................................... 62/4; 206/219
[51] Int. Cl.² ......................................... F25D 5/00
[58] Field of Search .................. 62/4; 206/219, 223; 126/263; 426/398

[56] References Cited
UNITED STATES PATENTS

| | | | |
|---|---|---|---|
| 2,714,974 | 8/1955 | Sawyer | 62/4 |
| 2,925,719 | 2/1960 | Robbins et al. | 62/4 |
| 3,887,346 | 6/1975 | Erdman | 62/4 |

FOREIGN PATENTS OR APPLICATIONS

| | | | |
|---|---|---|---|
| 580,807 | 8/1959 | Canada | 62/4 |
| 224,090 | 9/1959 | Australia | 62/4 |

Primary Examiner—Norman Yudkoff
Assistant Examiner—Frank Sever
Attorney, Agent, or Firm—Paul M. Denk

[57] ABSTRACT

In a thermal pack, one which may be provided with ingredients for making it either a cold pack or a hot pack, three bags are provided for the container of the pack, two of said bags being of the same size and comprising the exterior and proximate interior liners of the pack, while another bag of lesser dimensions forms the inner liner of said pack, and is disposed within the two larger bags. The inner bag is designed for holding a quantity of water, while the interior liner of the two outer bags is provided for holding a quantity of chemical means for use in varying the temmperature of the desired type pack. Rupturing of the inner bag through manual pressure allows water to react with the chemical means for creating either the cold or hot temperature, as needed.

8 Claims, 6 Drawing Figures

UREA COLD PACK HAVING AN INNER BAG PROVIDED WITH A PERFORATED SEAL

BACKGROUND OF THE INVENTION

This invention relates generally to a thermal pack, and principally one which may contain select ingredients in the nature of chemical means which when reacted with water provide either a cold or hot pack for medical or other usage.

Numerous types of packages are readily available in the prior art and upon the market for use for therapeutic purposes, and generally such packs are manufactured having separate compartments containing select discrete ingredients which when finally intermixed together, as through the introduction of one of the chemical ingredients with the other, there is provided either a refrigerated pack or a heat package. An example of the former is set forth in the U.S. Pat. to A. A. Robbins et al., No. 2,925,719, wherein a refrigerating packet is provided containing an outer and inner envelope, with the inner envelope containing water and the outer envelope containing a refrigerating chemical, such as ammonium nitrate, for reaction with the water when the inner envelope is broken. This concept of enveloping one package within the other is even older in the art, such as shown in the earlier U.S. Pat. to A. A. Robbins, No. 2,907,173. Other U.S. patents disclose the concept of forming a therapy package particularly for imparting heat, such as shown in the U.S. Pat. to Spencer, No. 3,542,032. In this latter patent the concept of creating a thermal reaction, i.e., for making a heat pack, is disclosed through the deposition of a quantity of urea within one compartment, while another compartment of the package is intended to be filed with water or a gel.

The present application while utilizing some of the teachings of these earlier prior art patents is designed to provide a particular chemical means for achieving either a thermal heat or refrigerating environment from a specially designed pack that is reinforced so as to prevent undue leakage of its ingredients during either shipment, storage, or usage.

It is therefore, the principal object of this invention to provide a therapy package for imparting a thermal reaction in the category of either a cooled or heated environment for use primarily in the treatment of animals.

It is another object of this invention to provide a thermal pack for use by humans, as for example, for for keeping warm as while attending a sporting event outdoors during the winter months.

Another object of this invention is to provide a compressible type of thermal pack that may be quickly caused to react by the consumer and without any resultant mess.

It is a further object of this invention to provide a thermal pack which may provide either instant heat or instant cold through the use of chemical ingredients which are nontoxic and noncaustic even should the user be exposed to its contents.

It is another object of this invention to provide a squeeze type pack which is significantly flexible to provide for its conformation to the surface to which it is applied for achieving maximum efficiency in the transfer of temperature to the treated area.

Another object of this invention is to provide a thermal pack which can be conveniently and immediately utilized in the treatment of animals, such as horses or the like.

These and other objects will become more apparent to those skilled in the art upon reviewing the summary of this invention, and in particular through a study of the description of the preferred embodiment in view of its drawing.

SUMMARY OF THE INVENTION

This invention contemplates the complete packaging of the various chemical components utilized in the formation of either a hot pack, or a cold pack, in a single thermal pack, which includes a series of enclosed bags, two of said bags comprising the outer liners of the pack, while a smaller dimensioned inner bag is enveloped therein. The inner bag, as are the two outer bags, are of some equivalent strength, so it can easily be seen that the inner bag itself will rupture upon the application of manual pressure when applied to all of said bags without the double strength combination of outer bags ever sustaining breakage. Hence, and as known in the art, the reaction chemicals utilized in the formation of thermal packs are generally separated from each other until the instance of usage, at which time one of the chemical bearing packages is broken for reacting it with another chemical to promptly initiate the type thermal reaction desired. It might be stated that throughout this application the word thermal is being used in an ambidextrous sense to mean a package which, depending upon its included contents, may form either a cold pack or a hot pack.

The hot pack of this invention preferably includes a quantity of water within the inner bag of the pack, with it being surrounded by a quantity of magnesium sulfate anhydrous which is included within the interior of the pair of outer bags of the pack. In addition, a small quantity of a coloring agent, such as for example any standard red dye that is readily available on the market, may be included with the quantity of water so as to provide it with some color, and which can be used for ready indentification of fact that the enclosed product comprises a hot pack. In addition, a quantity of granular material, such as sand, is included within the outer pair of bags, and intermixed with the magnesium sulfate anhydrous, and intended to add body to the pack, in addition to enhancing the heat retention characteristics of the pack for a more sustained period of time.

Various tests have been conducted with respect to the hot pack formulated in the manner as previously described and the following examples indicate the results of such experiments.

In the preferred pack, magnesium sulfate anhydrous has been included in an amount of approximately 83cc, and intermixed with a quantity of sand in amount of approximately 166cc. The combination of these two mixed ingredients are enclosed within the interior of the outer pair of bags, comprising the major liners of the hot pack. And, a quantity of water in the approximate amount of 119cc is sealed into the inner bag of the pack, and said bag along its upper seam was heat sealed into closure with the upper edges of the coextensive pair of outer bags or the major liners of this pack. Upon the application of a manual force to the combination of bags, particularly in a direction which causes a downward forcing of the water within the inner bag towards its lower marginal edge, said inner bag eventually ruptures, due to its having only one-half of the strength of the combined three bags making up the pack, thereby causing its contained water to immediately react with the magnesium sulfate anhydrous to achieve an exothermic reaction, generating heat and dispensing it for a prolonged period of time.

It might be stated that for the purpose of increasing the efficiency of operation of a hot pack formulated from these chemicals, that the magnesium sulfate anhydrous is of the type designed to have a 2% ignition point, i.e., known in the industry as a grade of anhydrous, and upon reacting with the water generates the heat somewhere in the vicinity of 182°F. for approximately 2 hours.

Various other combinations of these ingredients have been included and tested in the hot pack, and the following table indicates the various usages by volume of the designated ingredients for generating heat upon the reduction of the magnesium sulfate anhydrous with water.

| 1. | Magnesium sulfate anhydrous—119cc | | Water—119cc |
| 2. | Magnesium sulfate anhydrous and sand—277cc | | Water—92cc |
| 3. | Magnesium sulfate anhydrous—88cc | | Water—166cc |
| 4. | Magnesium sulfate anhydrous—221cc and sand | | Water—148cc |

The above examples of combination of these elements to induce the generation of an exothermic reaction was always effective, providing heat, as in test number 2, in the vicinity of 170°F. for approximately 1 hour, while in the fourth test heat was generated in the vicinity of 120°F for approximately three-fourths of an hour. The addition of sand in the tests number 2 and 4 is believed to retain the generated heat for a slightly greater length of time, due to the heat retention attributes of such a material. Usually the sand to magnesium sulfate anhydrous ratio is in the vicinity of 2/3 to 1/3.

The cold pack intended for usage in the style of formation of structure comprising the thermal package of this invention includes essentially the usage of the chemical urea within the interior of the pair of bags forming the major liners of this pack, while the third or inner bag comprising the minor liner of this invention is supplied independently, and separably, with a quantity of water. Also, the addition of some ammonium chloride has been found to enhance the endothermic functioning of this cold pack. In the preferred embodiment, 130cc of water is provided within the inner bag, while the quantity of urea provided in the outer pair of bags is in the vicinity of 250cc. Seventy cubic centimeters (cc) of the ammonium chloride is mixed with the urea. A pack formulated in this manner sustains a cold temperature in the vicinity of 12° to 19°F for approximately 1 hour or longer. In addition, a small quantity of dye, such as a blue dye, may be combined with the water so as to provide a ready identification of the nature of the thermal pack involved. The amount of dye added to either one of these packs may be in the vicinity of one-eighth teaspoonful per 20 gallons of water. Hence, a very small quantity of dye is needed simply for the purpose of providing a color indicia.

Another example of preparation of a cold pack under the teachings of this invention includes approximately 130cc of water within the inner bag, and 250cc of urea alone within the outer bag. A cold pack composed in this manner achieves a temperature in the vicinity of 34°F. for approximately 2 hours. Other examples of combinations of these ingredients utilized in a cold pack are set forth in the following table.

| 1. | Urea—130cc | | Water 130cc |
| 2. | Urea—260cc | | Water 130cc |
| 3. | Urea—500cc | Ammonium Chloride—500cc | Water 220cc |
| 4. | Urea—100cc | Ammonium Chloride—10cc | Water—45cc |

In the example number 1 set forth above the temperature of the cold pack, upon reaction, sustained 40°F for approximately 30 minutes. In example number 2, the reaction produced a temperature in the vicinity of 34°F. for approximately 1 hour.

In example number 3, which shows a maximum ingredient composition within a cold pack, a temperature of 0°F. was achieved for 2½ hours. And, finally, in the fourth experiment above, which is used for a first aid pack, and in the least ingredient composition, a temperature in the vicinity of 43°F. was maintained for approximately one-half hour.

BRIEF DESCRIPTION OF THE DRAWINGS

In the drawing, FIG. 1 provides a perspective view of the thermal pack of this invention.

DESCRIPTION OF THE PREFERRED EMBODIMENT

Figure 1:
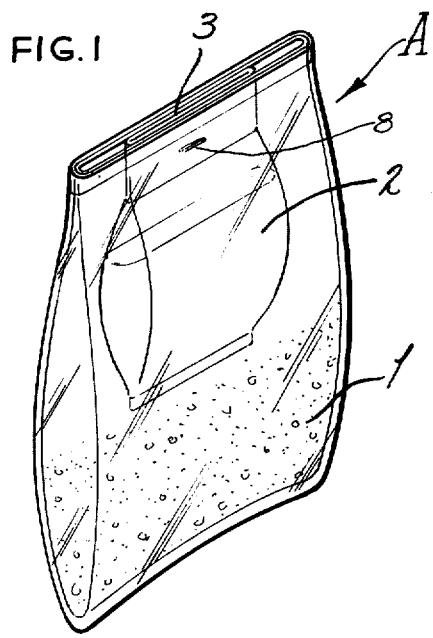

In referring to the drawing of this invention, there is shown in FIG. 1 the thermal pack A comprising the major liners 1, and a minor liner 2, respectively forming the outer an inner chemical holding bags of this invention. As can be seen, the upper marginal edges 3 of these bags are coextensive in width, being heat sealed together after insertion of their respective ingredients to provided sealed closure of this pack.

Figure 2:
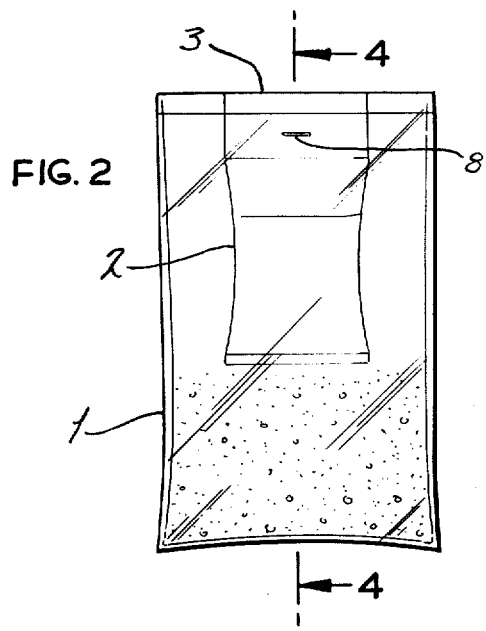
FIG. 2 provides a front surface view of the thermal pack shown in FIG. 1.
Figure 3:
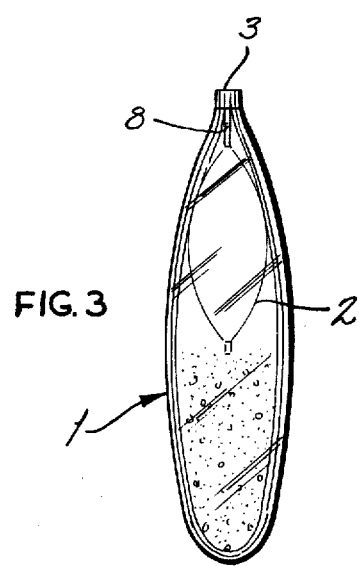
FIG. 3 provides a side edge view of the thermal pack shown in FIG. 1.
Figure 4:
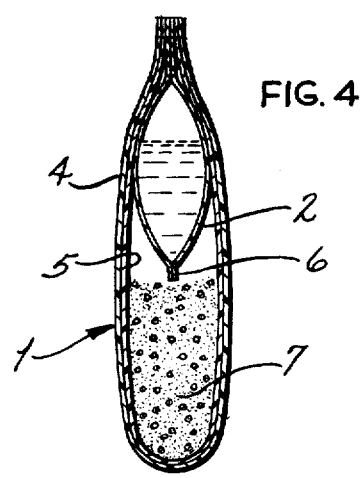
FIG. 4 provides a vertical sectional view taken along the line 4—4 of FIG. 2.
Figure 5:
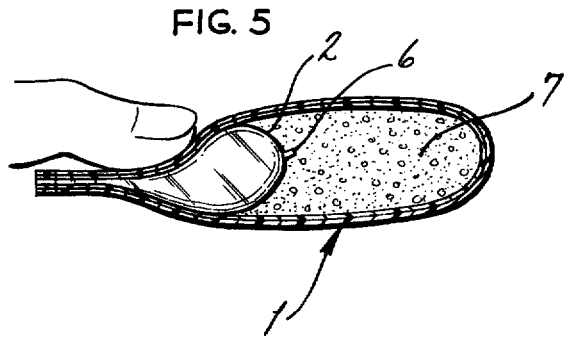
FIG. 5 provides a view of the thermal pack with manual force being applied to achieve rupturing of its inner bag.
Figure 6:
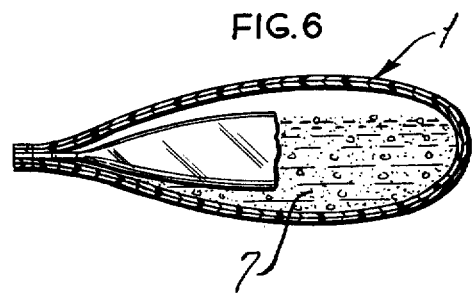
FIG. 6 discloses the reaction of the contents of the inner bag with the ingredients contained in the pair of outer bags to achieve temperature variation from the thermal pack of this invention.

By referring to FIG. 4, which is a sectional view taken of FIG. 2, the major liners of 1 of this invention comprises a pair of bags 4 and 5, with the combination of said bags being designed to form the exterior liner 4 and the just proximate major interior liner 5, to provide substantial reinforcement for this pack. All of these bags may be formed of thin tubular plastic material, such as from a polyethylene sleeve, and preferably is somewhat transparent to reveal its contents, and the coloring indicator. It can also be seen from this figure that the inner bag 2 is formed having a bottom marginal seal 6, which is intended to provide the means for focusing the position of the rupture to be made to this bag as when a force, such as the manual force shown being applied in FIG. 5, is exerted to rupture said inner bag 2 for dissemination of its contents with the contents 7 of the outer bags. As can be seen in FIG. 6, the inner bag 2 when ruptured directs its contents towards the disposed ingredients 7 of the bags 1, to initiate the thermal reaction. And, having the inner bag 2 sealed along the margin 3, with the outer bags, disposes its bottom margin approximately at the midpoint of said outer bags. As also shown in FIGS. 1 and 2, a perforation 8 in the side wall of the inner bag 2 is located just below the upper marginal seal of the thermal pack, although is within the seal of the said inner pack, and is provided for allowing a pressure relief at the time of manual activation of the liquid contained in the bag 2, to prevent the pressure of the liquid from being forced to act against the entire upper marginal seal and thus cause an untimely rupture of the pack at this location. Since the user customarily picks up a pack by its top margin, thereby depositing the contents of the outer bags downwardly of the same, forcing a rupture of the inner bag as shown in FIGS. 5 and 6 directs the flow of its contained water towards the accumulated chemicals. This achieves a quick mixture of the released water with the chemicals of the outer bags. Then, the intermixed and reacting chemicals can be spread evenly throughout the outer bags, a towel or cloth can be wrapped around the same, and the entire pack then applied directly to the affected area to be temperature treated.

As previously analyzed under the summary of this invention, the inner bag 2 usually is supplied with a quantity of water, and which water may be mixed or treated with a minute quantity of dye so as to provide means for publication of the type of thermal pack involved. In the preferred embodiment, a small quantity of red dye is added to the water for identifying the hot pack, while a small quantity of blue dye is added to the water in the inner bag 2 for identifying the cold pack.

In addition, and as also previously analyzed, the ingredients of the outer bags 1 vary depending upon the nature of the thermal pack desired, but in the preferred embodiment the outer bag 1 in the cold pack will be supplied with a major quantity of urea, with some of ammonium chloride being added, both of these ingredients being included in the amounts as previously reviewed in this application and as described in the table of formulations for a cold pack. Also, the ingredients included in the outer bags 1, when a hot pack is desired, comprise a quantity of magnesium sulfate anhydrous intermixed with a quantity of sand, or other granular material, that may enhance its heat retention, and both of these ingredients being included in the amounts as previously summarized in this invention.

Variations to the structure and ingredient formulations of the thermal packs of this invention may occur to those skilled in the art upon reviewing the description of this invention. Any such variations, if they are encompassed within the spirit and scope of the claims of this invention, are intended to be protected by any patent to issue thereon.

Having thus described the invention what is claimed and desired to be secured by Letters Patent is:

1. In a refrigerating pack for use in providing a decrease in temperature from the ambient temperature comprising a group of three pliable sleeve type plastic bags, two of said bags being of approximately the same size and strength and forming the exterior and contiguous interior major liners of the pack, an inner bag comprising a minor liner being formed as a sleeve type bag and having dimensions and strength substantially less than the combined major liners enveloping said inner bag, the upper marginal seams of said major and minor liners being co-extensive and sealed together to form the upper end of the pack, the lower end of the minor liner having a closing seam being capable of pressure rupture upon application of manual force, said inner bag having a seal extending below the upper marginal seams, the improvement which consists of a perforation provided through said inner bag within the seal provided below the upper marginal seams to provide a pressure relief at the time of activation of the pack to prevent the pressure from acting against the upper marginal seams and thereby cause rupture of the pack proximate said seams, the inner bag disposed for holding a quantity of water, the interior major liner disposed for holding a quantity of urea which upon reaction with said water provides for the decrease in temperature, the ratio by volume of the urea to water contained in the pack being between about a 1 to 1 ratio to a 2 to 1 ratio.

2. The invention of claim 1 wherein the urea is dried by heat prior to the deposition of said urea into the major interior liner of the pack to enhance its cold action.

3. The invention of claim 2 wherein the urea is dried through exposure to approximately 350° heat for approximately 1 hour.

4. The invention of claim 1 and further including a quantity of ammonium chloride being mixed with the urea in said cold pack.

5. The refrigerating pack of claim 1 wherein the urea and water are present in the following approximate percentages by volume:

| | |
|---|---|
| Urea | 50% to 70% |
| Water | 50% to 30%. |

6. The refrigerating pack of claim 5 wherein the ingredients are present in each pack within the range of the following approximate volumes:

| | |
|---|---|
| Urea | 100cc to 500cc |
| Water | 100cc to 220cc. |

7. The refrigerating pack of claim 6 and including as a further ingredient ammonium chloride in an amount arranging between about 10cc to 150cc.

8. The refrigerating pack of claim 7 wherein the ingredients are present in each pack in the following approximate volume:

| | |
|---|---|
| Urea | 250cc |
| Water | 130cc |
| Ammonium Chloride | 70cc | and said ingredients when mixed together being capable of sustaining a temperature of between about 12° to 25°F for approximately 2 hours.

* * * * *